United States Patent [19]

Rosenblum et al.

[11] Patent Number: 5,053,226
[45] Date of Patent: Oct. 1, 1991

[54] MONOCLONAL ANTIBODIES BINDING PLATINUM COMPLEXES

[75] Inventors: Michael G. Rosenblum; James L. Murray, both of Houston; Peter J. Kelleher, The Woodlands; Robert A. Newman; Abdul R. Khokhar, both of Houston, all of Tex.

[73] Assignee: Board of Regents, University of Texas System, Austin, Tex.

[21] Appl. No.: 73,500

[22] Filed: Jul. 15, 1987

[51] Int. Cl.$^5$ .................. A61K 39/40; A61K 39/42; A61K 39/44; C12N 5/00
[52] U.S. Cl. .................. 424/85.8; 424/86; 424/87; 435/240.27; 435/240.26
[58] Field of Search .................. 435/240.26, 240.27; 424/85.8

[56] References Cited

FOREIGN PATENT DOCUMENTS 0235457 9/1987 European Pat. Off. .
0263046 4/1988 European Pat. Off. .
83/03679 10/1983 World Int. Prop. O. .
86/01407 3/1986 World Int. Prop. O. .

OTHER PUBLICATIONS

Sundquist et al., Dec. 1987, Proc. Natl. Acad. Sci., 84:8225-8229, "Monoclonal Antibodies to DNA Modified with Cis- or Trans-Diamminedichloroplatinum (II)".
D. T. Reardan et al., Jul. 18, 1985, Nature, 316 (6025):275-268, "Antibodies Against Metal Chelates".
Goldenberg et al., (1980), *Science*, 208:1284-1286.
Goldenberg et al. (1980), *Cancer* 45:2500-2505.
Larson et al. (1983), *J. Nucl. Med.* 24:123-129.
Mach et al. (1980), *N. Engl. J. Med.* 303:5-10.
Kohler and Milstein, (1975), *Nature*, 256:495-497.
White et al. (1985), *Cancer Res.* 45:1337-1343.
Raso (1982), *Immunological Rev.* 62:93-117.
Raso et al. (1981), *Cancer Res.* 41:2073-2078.
Raso et al. (1983), *In Receptor-Mediated Targeting of Drugs*, 2, 10.
Raso et al. (1978), *Fed. Proc.*, 37:1350.
Gale (1975), *Antineoplastic and Immunosuppressive Agents* 38:829-840.
Rosenzweig et al. (1977), *Ann. Intern. Med.* 86:803-812.
Munchausen et al. (1975), *Cancer Chemother. Rep.* 59:643-646.
Dentino et al. (1978), *Cancer* 4:1274-1281.
Hill et al. (1975), *Cancer Chermother. Rep.* 59:647-659.
Daley-Yates, et al. (1984), *Biochem. Pharmacol.* 33:3063-3070.
Ghose et al. (1975), *Eur. J. Cancer* 11:321-326.
Moshakis et al. (1981), *Br. J. Cancer* 43:575-581.
Sullivan et al. (1982), *Invest. Radiol.* 17:350-355.
Ramakrishnan et al. (1984), *Cancer Res.* 44:1398-1404.
Embleton (1983), 3H Brit. J. Cancer, 47:43-50.
Thorpe (1981), *Eur. J. Biochem.*, 116-447-454.
Gallego et al. (1984), *Int. J. Cancer*, 33:737-744.
Fitzgerald et al. (1984), *J. Clin. Invest.*, 74:966-971.
Drobnik (1983), *Cancer Chemother. Pharmacol.*, 10:145-149.

(List continued on next page.)

*Primary Examiner*—Johann Richter
*Attorney, Agent, or Firm*—Arnold, White & Durkee

[57] ABSTRACT

The present invention relates to monoclonal antibodies specifically binding platinum (II) complex. The monoclonal antibodies of the present invention are characteristically produced by antibody-producing cell lines such as hybridomas. These cell lines may result, for example, from fusion of a neoplastic cell with an antibody-producing animal cell obtained from an animal immunized against a platinum (II) complex. The cellular fusion products include cell lines forming monoclonal antibody specifically binding platinum (II) complex in competition with an antibody produced by: hybridoma strain $1C_1H_2A_5$, deposited with the American Type Culture Collection, Rockville, MD on May 1, 1987 and having ATCC accession number HB 9411; strain $3A_2A_1$; strain $1A_6A_2$; strain $3A_6B_1$ or strain $1B_1$. The cell lines of the present invention are preferably continuous murine hybridoma cell lines which secrete recoverable quantities of monoclonal antibody, particularly a monoclonal antibody which is of an IgG or IgM isotype.

20 Claims, 6 Drawing Sheets

OTHER PUBLICATIONS

Gilman et al. (1980), *The Pharmacological Basis of Therapeutics*, 1249–1313.
Blythman et al. (1981), *Nature*, 290:145–146.
Moolten et al. (1970), *Science*, 169:68–70.
Hurwitz et al. (1975), *Cancer Res.*, 35:1175–1181.
Kato et al., (1984), *Cancer Res.*, 44:25–30.
Ghose et al. (1978), *J. Natl. Canc. Inst.* 61:657–676.
Carlsson et al. (1978), *Biochem. J.*, 173:723–727.
Stirpe et al. (1980), *J. Biol. Chem.* 255:6947–6953.
Greenfield et al. (1985), *Proc. Amer. Assoc. Cancer Res.* 26:336.
Webb et al. (1985), *Proc. Amer. Assoc. Cancer Res.* 26:272.
Ghose et al. (1972), *Cancer*, 29:1398–1400.
Wattenburg (1985), Cancer Res. 45:1–8.
Sherwood (1970), New Eng. J. Med. 283: 1150–1156.
Raso and Basala (1983), In Receptor-Mediated Targeting of Drugs.
Articles Related to Monoclonal Antibodies Specific for Digoxin.
Herwitz (1983), Biopolymers 22:557–567.

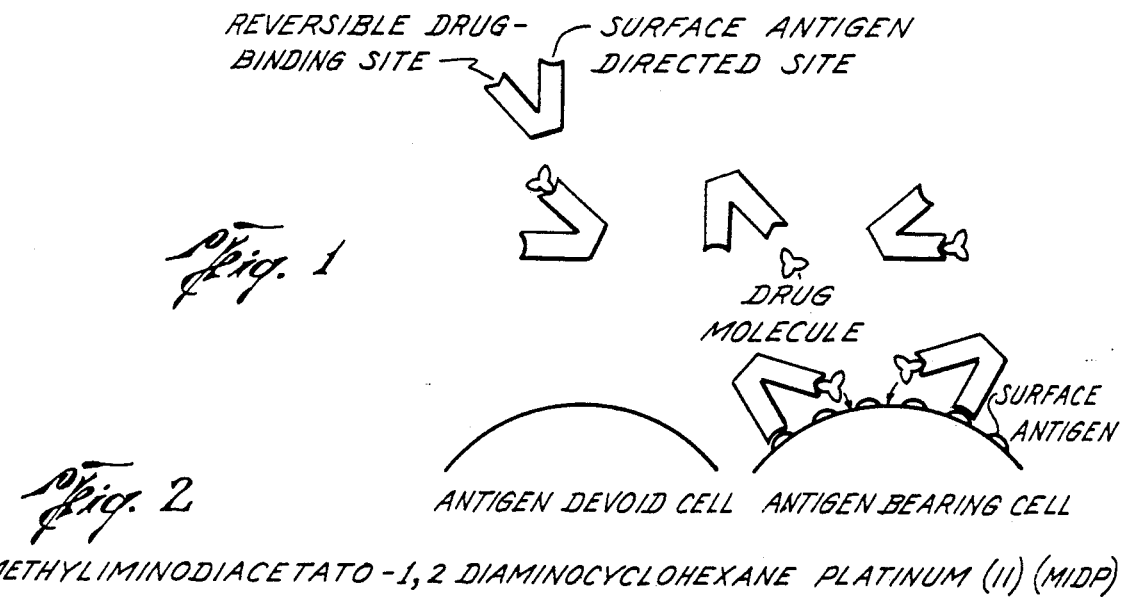
Fig. 1
Fig. 2
METHYLIMINODIACETATO-1,2 DIAMINOCYCLOHEXANE PLATINUM (II) (MIDP)
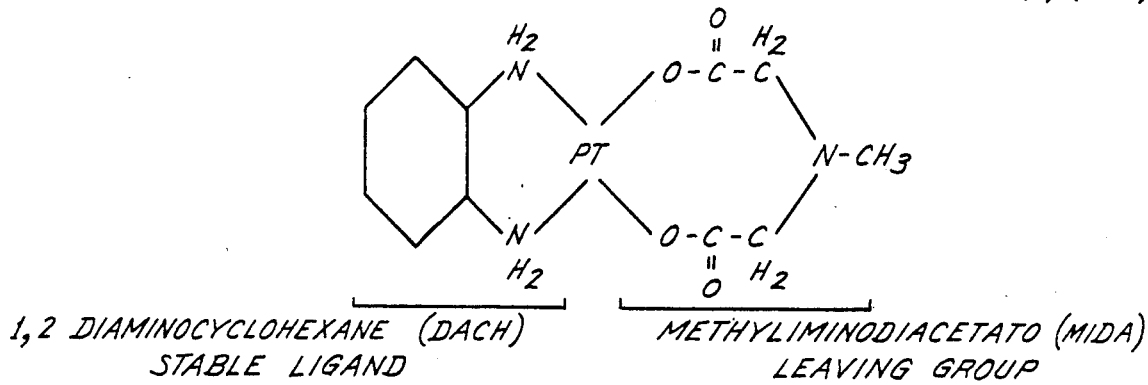
1,2 DIAMINOCYCLOHEXANE (DACH)
STABLE LIGAND
METHYLIMINODIACETATO (MIDA)
LEAVING GROUP
SULFATO 1,2-DIAMINOCYCLOHEXANE PLATINUM (II)
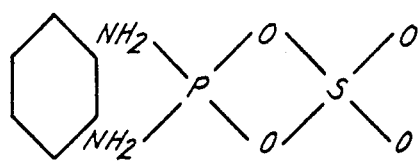
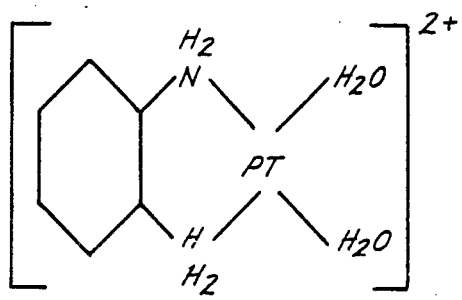
1,2 DIAMINOCYCLOHEXANE (DACH) PLATINUM (II) (2)

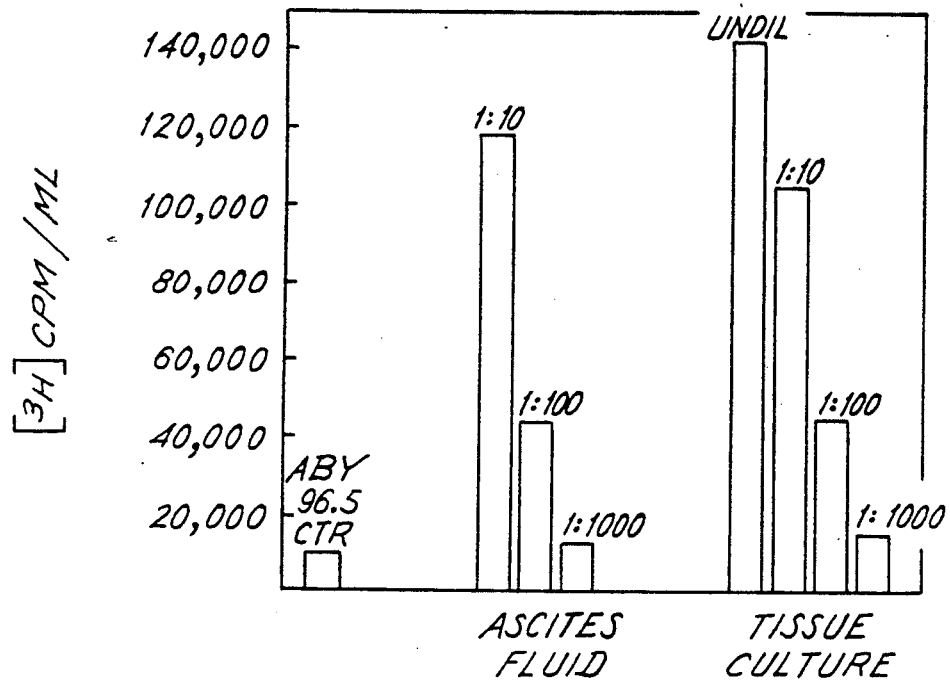
Fig. 3 EQUILIBRIUM DIALYSIS OF ABY $1C_1H_2A_5$ WITH $[^3H]$ DACH PT
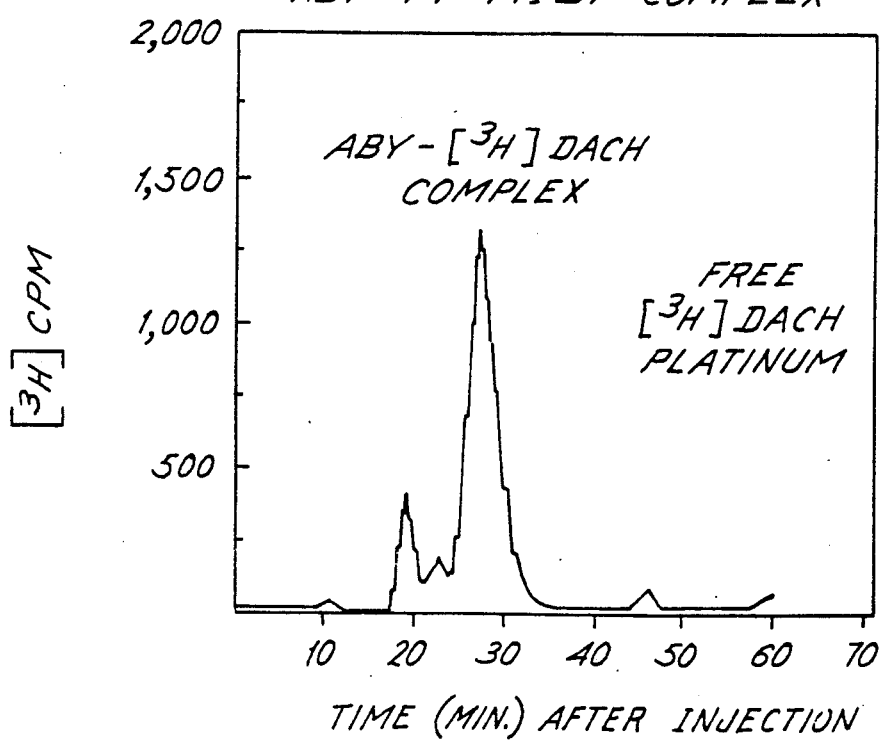
Fig. 4 HIGH PRESSURE LIQUID CHROMATOGRAPHY OF ABY-PT-MIDP COMPLEX

MONOCLONAL ANTIBODIES BINDING PLATINUM COMPLEXES

BACKGROUND OF THE INVENTION

The present invention relates to monoclona antibodies directed toward platinum (II) complexes, their preparation and uses such as carrying platinum (II) complexes to tumor.

Murine monoclonal antibodies directed toward antigenic determinants expressed on the surface of human tumor cells have the potential to selectively localize in tumors after systemic administration (Goldenberg et al., Science 208:1284–1286, (1980); Goldenberg et al., Cancer 45:2500–2505, (1980); Larson et al., J. Nucl. Med., 24:123–129, (1983); Mach et al., N. Engl. J. Med., 303:5–10, (1980)). This property has been successfully exploited due to recent advances in hybridoma technology which have made available large amounts of purified, high-specificity murine monoclonal antibodies directed toward a wide variety of human tumor-associated cell-surface antigens (Kohler and Milstein, Nature, 256:495–497, (1975); White et al., Cancer Res., 45:1337–1343, (1985); Morgan et al., Hybridoma, 1:27–36 (1981)).

Previous studies by Raso et al., utilizing in vitro and in vivo animal models, have demonstrated that a variety of drugs and toxins, including the A chain from the plant toxin ricin and the antitumor antibiotic agent neocarcinostatin, can be successfully targeted to human tumor cells (Raso, Immunological Rev., 62:93–117 (1982); Raso et al., Cancer Res., 41:2073–2078 (1981); Raso et al., In Receptor-Mediated Targeting of Drugs: NATO Advanced Studies Institute, Gregoriadis (ed), V 2, Plenum Press, NY (1983); Raso et al., Fed. Proc., 37:1350 (1978).

The cytotoxic potential of platinum coordination complexes was first discovered in the mid-sixties (Rosenberg et al., Nature, 205:698–699 (1965)). cis-Diaminedichloro-platinum (II) (cisplatin) was identified in experimental tumor systems as the most active of these compounds (Rosenberg, Naturwissenschaften, 60:399–406 (1973)). This unique inorganic chemotherapeutic drug is utilized as a first-line agent in the treatment of metastatic testicular and ovarian carcinomas, in combination chemotherapy for the treatment of carcinomas of the head and neck and bladder (Gale, In: *Antineoplastic and Immunosuppressive Agents*, Pt. II, Sartorelli et al., (eds), Handbuch der Experimentellen Pharmakologie, 38:829–840 (1975); Rosenzweig et al., Ann. Intern. Med., 86:803–812 (1977)), and is constantly introduced into new treatment protocols. The cell nucleus is thought to be the most important site for the drug's cytotoxic activity; when cisplatin enters a cell, two highly reactive ligand sites are formed as a result of chloride ion hydrolysis. These sites react with DNA to form inter- and intrastrand crosslinks which disrupt and unwind portions of the double helix (Munchausen et al., Cancer Chemother. Rep., 59:643–646 (1975)).

The clinical use of platinum complexes is associated with a high incidence of serious, dose-limiting toxic side effects arising as a consequence of the high chemical liability and non-tumor tissue deposition of platinum complexes. Renal distal tubular damage and neurotoxic effects, including peripheral neuropathies, have been described (Dentino et al., Cancer, 4:1274–281 (1978); Bourne, Austr. J. Audiology, 6:33–80 (1984)). The severity of these side effects has provided the impetus for the synthesis of second and third generation analogues with decreased toxicity and increased aqueous solubility and stability.

One third generation compound, methyliminodiacetato-1,2-diaminocyclohexane platinum (II) (MIDP; schematically described in FIG. 2) has been shown, with multi-dose administration, to be curative in the treatment of L1210 leukemia and $B_{16}$ melanoma in mice. At doses with equipotent antitumor efficacy as compared to cisplatin,, MIDP apparently does not induce renal toxicity in animal models. Additionally, cells resistant to cisplatin have been shown by others not to display cross-resistance to MIDP. Thus, MIDP appears to have an advantage over the parent platinum (II) compound, i.e., retaining antitumor efficacy and potency with the diminution of toxic side effects.

The antitumor activity of platinum complexes arises as a consequence of their chemical nature, as does a high degree of non-specific reactivity. More than 90% of cisplatin in plasma is tightly bound to plasma protein, leading to a prolonged plasma half-life of bound, inactive drug (Hill et al., Cancer Chemother. Rep., 59:647–659 (1975). The remaining unbound, highly reactive drug can participate in a number of hydrolytic and degradative reactions in plasma; the metabolites formed have greater nephrotoxic potential and decreased antitumor activity (Daley-Yates et al., Biochem. Pharmacol., 33:3063–3070 (1984)). Thus, the inherent reactivity of the platinum molecule may compromise distribution to the tumor site and, therefore, antitumor efficacy. The next logical goal in the development of effective platinum analogues and object of the present invention is to solve the problem of non-tumor associated reactivity and to increase deposition within the tumor.

A variety of murine monoclonal antibodies have been developed which recognize antigens present on the surface of human tumor cells. A number of these demonstrate minimal reactivity to normal (nonmalignant) tissues and have been utilized for tumor imaging as well as for delivery of drugs and toxins to tumor tissue (Ghose et al., Eur. J. Cancer, 11:321–326 (1975); Goldenberg et al., Science, 208:1284–1286 (1980)). Various imaging studies have indicated that tumor may accumulate two to ten times more radiolabeled monoclonal antibody than non-target tissue (Moshakis et al., Br. J. Cancer, 43:575–581 (1981); Sullivan et al., Invest. Radiol., 17:350–355 (1982)). Thus, an antitumor agent bound or coupled to a monoclonal antibody may not only exhibit increased tumor distribution but also altered clearance and systemic effects. A purpose of the delivery system of the present invention is to utilize murine monoclonal antibodies for favorably modifying the pharmacology and, tissue disposition and efficacy of platinum complexes.

There are generally two types of monoclonal antibody complexes that could be prepared for utilization in drug delivery systems. In the first, for example, a tumor targeting antibody may be directly coupled to a drug, forming an irreversible covalent complex. In the second, a monoclonal antibody capable of reversibly binding a drug may be covalently coupled to an antibody recognizing a tumor-associated antigen. The direct coupling approach has been utilized for a number of therapeutic agents such as adriamycin, vindesine and methotrexate as well as plant and bacterial toxins, including ricin A chain, pseudomonas exotoxin, pokeweed antiviral protein and gelonin (Ramakrishnan et al., Cancer Res., 44:1398–1404 (1984; Hurwitz et al/., Ann. NY Acad. Sci., 417:125–136 (1983); Embleton [$^3$H] Brit. J. Cancer, 47:43–50 (1983); Thorpe et al., Eur. J. Biochem., 116:447–454 (1981); Bjorn et al., Cancer Res., 45:1–8 (1985); Gallego et al., Int. J. Cancer, 33:737–744 (1984); Fitzgerald et al., J. Clin. Invest., 74:966–971 (1984)). These studies concluded that direct conjugates were efficacious both in vitro and in vivo, increasing cytotoxic agent delivery and having enhanced cytotoxicity as compared to free drug or toxin. The use of direct coupling procedures, however, may result in an adverse modification of the drug or toxin such that a significant portion of the coupled molecules are inactivated. Also, covalent modification of monoclonal antibodies may disturb antibody conformation and can lead to a decreased affinity for the binding site. The high chemical liability of platinum complexes and the finding that slight chemical modification of this agent can lead to its inactivation eliminate the desirability of using a direct covalent coupling approach for platinum (II) complex antibody delivery systems (Fitzgerald et al., J. Clin. Invest., 74:966–971 (1984); Kerrison et al., J. Chem. Soc./Chem. Comm., 27:861 (1977); Drobnik, Cancer Chemother. Pharmacol., 10:145–149 (1983).

Many chemotherapeutic agents suffer shortcomings which limit or complicate their use. Pharmacology studies, for example, show that some agents may be: cleared rapidly from the circulation; extensively distributed to non-tumor tissue compartments; complexed irreversibly with endogenous plasma components; or metabolically inactivated by plasma or tissue enzymes (Gilman et al., The Pharmacological Basis of Therapeutics, Ed. 6, pp 1249–1313 (1980) Macmillan publishing Co., NY; Carter et al., (eds) Principles of Cancer Treatment, pp 1–951 (1982) McGraw-Hill, NY; Camiener, Biochem. Pharmacol., 16:1398–1400 (1972)). All of these dynamic events can severely reduce the amount of biologically active drug available to the tumor. The exploitation of specific monoclonal antibody binding characteristics to confer a high degree of selectivity for indiscriminately cytotoxic drugs and toxins is an attractive possibility and part of the present invention.

Antitumor agents coupled directly to monoclonal antibodies have been proposed before (Ghose et al., Cancer, 29:1398–1400 (1972); Calendi et al., Boll. Clin. Farm., 108:25–28 (1969)). They were envisioned as unique and specific protein carriers to favorably modify the pharmacology of antitumor agents such as toxic drugs by directing these agents to tumors while reducing their distribution to sites of potential toxicity (Blythman et al., Nature, 290:145–146 (1981). previous approaches to conjugating monoclonal antibodies with either toxins or chemotherapeutic agents utilized direct covalent coupling reactions or bifunctional cross-linking reagents to attach agents or toxins tightly to an antibody carrier molecule (Hurwitz et al., Ann. NY Acad. Sci., p 125 (1983); Moolten et al., Science, 169:68–70 (1970)). Problems associated with this covalent coupling approach, as mentioned above, may result from the covalent modification of murine antibodies disturbing antibody integrity and modifying antigen recognition sites of the antibody. In addition, covalent modification of some active therapeutic agents may significantly reduce or completely ablate their antitumor efficacy (Hurwitz et al., Cancer Res., 35:1175–1181 (1975); Kato et al., Cancer Res., 44:25–30 (1984). In many cases, the full expression of biological activity of cytotoxic agents may be hindered by covalent coupling to a carrier such as an antibody. For example the antiproliferative activity of such covalently altered complexes may depend on: 1) extracellular hydrolytic or enzymatic release of the active agent from the conjugate at the tumor site (Ghose et al., J. Natl. Canc. Inst., 61:657–676 (1978); or 2) internalization and intracellular cleavage of the stable bond between the active agent and the antibody (Bjorn et al., Cancer Res., 45:1–8 (1985). Hydrolytic or enzymatic release of cytotoxic agents from covalent complexes at the tumor site may not be uniformly dependable. Degradation of the complex by enzymes present in plasma may provide premature release of the active agent and thereby compromise further the therapeutic efficacy of these covalent complexes.

The utilization of highly specific antigen recognition sites of antibodies to tightly yet reversibly bind therapeutic agents in a non-destructive fashion is a potentially attractive alternative to these covalent coupling methods and is a feature of the present invention. An object of this invention is to describe a novel, tumor-targeted antibody drug delivery system consisting of a monoclonal antibody capable of reversibly binding a therapeutic agent in combination with an antibody recognizing a tumor-associated antigen. This novel approach for reversibly coupling therapeutically active agents to tumor-targeting antibodies represents a route to circumvent some of the difficulties posed by conventional covalent coupling of active agents directly to monoclonal antibodies. In this approach the monoclonal antibody delivery system contains a reversible, drug-binding site, as schematically shown in FIG. 1. This may be accomplished by producing a carrier monoclonal antibody to the active agent and coupling this carrier to a tumor-targeting antibody. Such coupling may be accomplished, for example, by using a heterobifunctional cross-linking reagent to generate an antibody-antibody linkage (Bjorn et al., Cancer Res., 45:1–8 (1985); Carlsson et al., Biochem. J., 173:723–727 (1978).

Advantages of this type of delivery complex over one involving the covalent linkage of drugs to antibodies include, for example:

1) The affinity of the complex for the active agent can be varied by selecting anti-drug antibodies with desired affinity constants (Ka), thereby subtly altering the exchange properties of the active agent with the targeting site. This should change the efficiency with which a complex delivers cytotoxic agents to target sites. Rapidly-reversible (lower affinity) complexes may be important for quick release of low molecular weight cytotoxic agents at the tumor surface to allow more rapid transport of the agent across the cell membrane and interaction at its site of action without the hindrance of an attached, high molecular weight carrier protein. Higher affinity complexes which result in slow or minimal release of active agents may be important for the delivery of toxins such as gelonin. This particular agent should remain coupled since the antibody complex acts as both a cell-targeting carrier and an internalization mechanism to allow the toxin to localize on tumor cells and to cross mammalian cell membranes for interaction with ribosomal structure, respectively (Stirpe et al., J. Biol. Chem., 255:6947–6953, (1980).

2) The active agent itself is not subjected to chemical modification. This is of exceptional importance in attempting to target cytotoxic agents such as platinum complexes, with a definitive structure activity relationship (SAR) or chemical liability.

3) Once an appropriate drug-carrier antibody is generated and the covalent carrier antibody:antibody tumor-specific cross-linking conditions have been well-defined, a large library of reversibly agent-binding tumor targeting antibody complexes may be produced. New complexes may be generated, for example, by using tumor targeting antibodies directed to different epitopes of the same cell surface antigen, antibodies to different surface antigens present on the same cell type or using antibodies to target different tumor types of interest.

The reversible drug-binding delivery system approach may allow the specific delivery of reversibly-coupled, unmodified agents such as MIDP to tumors. This type of delivery system is schematically shown in FIG. 1. Previous studies by Raso et al. have demonstrated that this non-covalent targeting approach should be effective (Raso et al., Fed. Proc., 37:1350 (1978); Raso et al., Cancer Res., 41:2073–2078 (1981); Raso, Immunological Rev., 62:93–117 (1982); Raso et al., In Receptor-mediated Targeting of Drugs: NATO Advanced Studies Institute, Gregoriadis (ed), V 2, Plenum Press, NY (1983) in press). Neocarzinostatin, an antitumor antibiotic, and the A-chain of ricin were delivered to tumor cells in vitro by means of reversibly binding antibody:antibody complexes. The ricin A chain-binding antibody:antibody complex was found to specifically deliver ricin to antigen-bearing target cells. This ricin-bearing complex was also shown to substantially inhibit cell growth and lead to cell death. The ricin:antibody complex was found to be 5000 times more potent compared to ricin A chain alone. The in vivo pharmacokinetics of the ricin A chain:antibody complex and free ricin A chain were examined in rabbits.

Administration of ricin:antibody conjugate led to a prolongation of the beta-phase half-life for complexed ricin as compared to free ricin alone.

Further advantages of the reversible drug-binding delivery approach of the present invention as compared to directly coupled complexes may be described in regard to MIDP as follows:

(1) Much greater flexibility is possible. For example, the diaminocyclohexane ring of MIDP represents a chemically stable portion of the molecule to which antibodies may be directed. Monoclonal antibodies described herein with varying affinities for MIDP have been isolated and could be utilized for the preparation of antibody-MIDP complexes. This will allow evaluation of the relationship of drug delivery efficiency to alterations in the affinity constant for drug binding.

(2) Flexibility should also be possible in the selection of the drug to be carried by antibodies reactive, for example, to the DACH ring of MIDP. These antibodies should also recognize a variety of other third generation platinum analogues which also contain the DACH ring. Thus, a number of different platinum complexes may be evaluated for tumor delivery for each targeting antibody:carrier antibody conjugate prepared.

(3) Drug carried to the tumor by such a reversibly-binding antibody:antibody complex is not chemically modified; bound molecules may represent a future pool of free, active drug.

(4) After selection of an optimal drug-binding(carrier) antibody, conjugates with various targeting antibodies may be made. This flexibility will allow a panel of antibody complexes to be prepared, all directed towards a specific tumor type or a number of tumor types.

(5) The activity of direct covalently-coupled complexes may be highly dependent on the extent of drug-antibody cell surface receptor internalization. Reversible drug-binding complexes may act quite differently; free, active drug may also be released and be available for interaction with the cell surface. Evidence is steadily accumulating that the process of antibody-binding to the cell surface may alter membrane conformation; sensitization to subsequently administered therapeutic agents may ensue (Greenfield et al., Proc. Amer. Assoc. Cancer Res., 26:336 (1985); Webb et al., Proc. Amer. Assoc. Cancer Res., 26:272 (1985)). Free MIDP, released from antibody complexes at or near the cell surface, may act in this manner. Therefore, the reversible drug-binding antibody complexes of the present invention may represent a first step in the development of a new class of novel chemotherapeutic agents with multiple mechanisms and sites of action. Further studies with MIDP should provide insights into the optimization and future utilization of this approach for the delivery of other therapeutic agents, biological modifiers and toxins.

A broad object of the present invention is to utilize a novel, specific monoclonal antibody to reversibly bind therapeutic platinum (II) complex. Other potential uses of this antibody also include but are not limited to:

1) A composition in which a reversible-binding antibody is utilized to extend the short plasma half-life and therapeutic action of a Pt complex.

2) A composition in which an antibody specific for a Pt (II) complex itself or a specific Pt (II) complex is utilized in an enzyme-linked immune-absorbent (ELISA) assay for quantitation of platinum or platinum complex in urine, serum, other biological fluids or tissues.

3) The use of antibodies specifically binding platinum (II) complex antibodies as specific probes to detect platinum complexes at the cellular or sub-cellular level.

Many other objects and advantages of the present invention too numerous to list herein are inherent in the presently described invention.

SUMMARY OF THE INVENTION

The present invention relates to monoclonal antibodies specifically binding platinum (II) complex, most preferably a DACH platinum II complex. The monoclonal antibodies of the present invention are characteristically produced by antibody-producing cell lines such as hybridomas. These cell lines may result, for example, from fusion of a neoplastic cell with an antibody-producing animal cell which may be obtained from an animal immunized against a platinum (II) complex. The cellular fusion products include cell lines forming monoclonal antibody specifically binding DACH platinum (II) complexes in competition with an antibody produced by: hybridoma strain $1C_1H_2A_5$, deposited with the American Type Culture Collection, Rockville, MD on May 1, 1987 (tested as viable May 7, 1987) and having ATCC accession number HB 9411; strain $3A_2A_1$; strain $1A_6A_2$; strain $3A_6B_1$ or strain $1B_1$ (the latter four strains being available to the Commissioner of Patents and Trademarks from the inventors' stock cultures during the pendency of this application). The cell lines of the present invention are preferably continuous murine hybridoma cell lines which secrete recoverable quantities of monoclonal antibody, particularly a monoclonal antibody which is of an IgG or IgM isotype. The antibodies may be those produced by the above-referenced hybridoma strains.

In a preferred aspect of the present invention, the cell line which produces monoclonal antibody specifically binding platinum (II) complex is produced by fusion of a neoplastic cell such as a myeloma cell with an antibody-producing animal cell such as a splenic cell. An antibody-producing animal cell is obtained from an animal immunized against platinum (II) complex. An animal such as a mouse, for example, may be immunized against a platinum (II) complex by a process involving immunization with a platinum (II) complex coupled to a carrier. An immunized animal may be produced by a process involving immunization with a conjugate of a platinum (II) complex and a macromolecular species, for example, a protein or a polynucleotide such as DNA. A preferred platinum (II) complex of the present invention is a 1,2-diaminocyclohexane (DACH)-platinum complex. The platinum (II) complexes of the present invention are most commonly usable as antitumor agents but may have other biological or therapeutic activity. The term "platinum (II) complex," as used subsequently herein, may be understood as a DACH platinum (II) complex unless otherwise specified.

The cell lines of the present invention include hybridoma strain $1C_1H_2A_5$ having ATCC accession number HB 9411, strain $3A_2A_1$, strain $1A_6A_2$, strain $3A_6B_1$ and strain $1B_1$. A murine hybridoma cell line, for example, one of the above strains, secreting recoverable quantities of a monoclonal antibody which specifically binds a platinum (II) complex exemplifies a central aspect of the present invention.

A composition of matter comprising a monoclonal antibody such as one described above which specifically binds a platinum (II) complex is within the scope of the present invention. This composition of matter may be defined further as comprising a monoclonal antibody which binds a platinum (II) complex in competition with an antibody produced by one of the cell lines of the present invention. The monoclonal antibody of this composition of matter may be, for example, of an IgG or IgM isotype and be one actually produced by a cell line of the present invention.

An antibody which is competitive for binding to a platinum (II) complex with monoclonal antibody from a cell line of the present invention may readily be identified by methods well-known to those skilled in the relevant arts upon examination of the present application. For example, a platinum complex could first be immobilized upon a solid matrix as described elsewhere herein. A monoclonal antibody from a cell line of the present invention may be labeled with a detectable label such as an enzyme, radioisotope or chromophore. The immobilized platinum complex would then be treated with an aqueous solution of the potentially competitive antibody or with a control aqueous solution devoid of potentially competitive antibody. After washing the treated immobilized platinum complex, the immobilized platinum complex would be exposed to a solution of the labeled monoclonal antibody of the present invention. A decrease in detectable label bound to the immobilized platinum complex which is attributable to treatment with the potentially competitive antibody would indicate that the potentially competitive antibody was indeed competitive for binding to the platinum complex.

The present invention may involve a method for increasing the circulating half-life and therapeutic effectiveness of a platinum (II) complex parenterally administered to an animal. This method comprises parenteral administration to the animal of a quantity of monoclonal antibody as described above having specific binding affinity for platinum (II) complexes. The platinum (II) complex and the monoclonal antibody would combine in an antibody-antigen combinant. Formation of an antibody-antigen combinant of monoclonal antibody and platinum (II) complex should prevent the platinum (II) complex from being rapidly removed from circulating blood by ordinary modes of drug clearance. The platinum (II) complex and the monoclonal antibody may be parenterally administered in a preformed combination or separately administered to form a combinant in vivo.

In a further aspect, the present invention may involve a composition of matter which is specifically directed toward a tumor target site. Such a composition of matter would comprise, for example, in addition to a first monoclonal antibody directed toward a platinum (II) complex, a second monoclonal antibody which specifically binds to a tissue target site. The second monoclonal antibody is preferably covalently bound to the first monoclonal antibody. Again, the first monoclonal antibody may be a monoclonal antibody produced by a cell line of the present invention may be competitive with this monoclonal antibody for binding to a platinum (II) complex such as a DACH-platinum (II) complex.

The amount of a platinum (II) complex present in a biological sample may be determined by processes of the present invention. One such process could comprise a series of steps which may be described as follows. A first monoclonal antibody which has a first isotype and specifically binds platinum (II) complex would be immobilized. The immobilized antibody would then be contacted with the biological sample, for example in aqueous solution, whereupon any platinum (II) complex in the biological sample would bind to the immobilized antibody. The contacted immobilized antibody would then be washed essentially free of unbound biological sample. The immobilized first monoclonal antibody would then be treated with a second monoclonal antibody, the second monoclonal antibody having a second isotype and specifically binding the platinum (II) complex. After washing the immobilized first monoclonal antibody essentially free of unbound second monoclonal antibody, it would be treated with a labeled antibody having an affinity for antibody of the second isotype. Finally, the amount of labeled antibody bound to the immobilized antibody would be measured by observation of the label as an index of the amount of platinum (II) complex present in the biological sample.

Additional possible methods for determination of platinum (II) complex amounts in biological samples are provided within the scope of the present invention. One such additional method would involve immobilizing a platinum (II) complex upon a solid matrix such as that of a bead or wall, for example. A first monoclonal antibody of a first animal species which specifically binds platinum (II) complex would be incubated with the biological sample under study. The immobilized platinum (II) complex would then be contacted with fresh first monoclonal antibody or with the incubated first monoclonal antibody so that monoclonal antibody with an unoccupied binding site for platinum (II) complex binds to the immobilized platinum (II) complex. Unbound biological sample would then be removed from the immobilized platinum (II) complex, for example by washing. The washed immobilized platinum (II) complex would then be contacted with a labeled antibody having an affinity for antibodies of the first animal species. The amount of labeled antibody bound to the immobilized platinum (II) complex would finally be measured through its label. Any decrease in the amount of labeled antibody binding to the immobilized platinum (II) complex which is due to incubation with the biological sample would be an index of the amount of platinum (II) complex present in the biological sample.

Other "sandwich"-type or competitive immunoassays for determining the amount of platinum (II) complex present in a biological sample are possible using the monoclonal antibodies of the present invention. An example of one such method would comprise: a) immobilizing a first monoclonal antibody specifically binding a platinum (II) complex; b) incubating the immobilized first antibody with the biological sample; c) washing the immobilized first monoclonal antibody essentially free of unbound biological sample; d) contacting the washed immobilized first monoclonal antibody with a second monoclonal antibody specifically binding said platinum (II) complex and bearing a detectable label; e) washing the immobilized antibody essentially free of unbound second monoclonal antibody; and f) measuring the amount of detectable label bound to the immobilized antibody as an index of the amount of platinum (II) complex present in the biological sample.

The present invention further comprises methods for detecting the presence of platinum (II) complex in a biological sample at the cellular or subcellular level. These methods may frequently involve microscopic examinations of biological samples and the specific localization of detectable labels. One such method would involve: a) treating a biological sample with a first monoclonal antibody specifically binding platinum (II) complex and bearing a detectable label and b) determining the amount and location of detectable label bound to cellular and subcellular components of the biological sample.

Another method for detecting the presence of platinum (II) complex in a biological sample at the cellular or subcellular level would comprise: a) treating said biological sample with a first monoclonal antibody specifically binding said platinum (II) complex and derived from a first animal species; b) washing the biological sample essentially free of unbound first monoclonal antibody; c) treating the biological sample with an antibody bearing a detectable label and having a binding affinity for antibodies of the first animal species; and d) determining the amount and location of detectable label bound to cellular and subcellular components of the biological sample.

Variations of these methods for detecting the presence of a platinum (II) complex in a biological sample at the cellular or sub-cellular level would be readily apparent to those skilled in the art upon examination of the present application. One other variant, for example, would comprise: a) treating a biological sample with a first monoclonal antibody specifically binding platinum (II) complex and having a specific isotype; b) washing the biological sample essentially free of unbound antibody; c) treating the biological sample with an antibody bearing a detectable label and having a binding affinity for the specific isotype of the first monoclonal antibody; and d) determining the amount and location of detectable label bound to cellular and subcellular components of the biological sample, preferably by microscopic means.

In all the above described methods involving monoclonal antibodies the first monoclonal antibody is one of the present invention or competitive for binding to platinum (II) complex with a monoclonal antibody of the present invention. The second monoclonal antibody, when specific for platinum (II) complexes used in practicing methods of the present invention preferably is of the same description as the first monoclonal antibody. The platinum (II) complexes utilized in the practice of the methods of the present invention, as mentioned before, preferably are DACH-platinum (II) complexes.

In yet another aspect, the present invention involves methods for the production of monoclonal antibodies specifically binding to a platinum (II) complex, particularly a cis DACH platinum complex. One such method comprises the steps of: a) parenterally administering a conjugate comprising haptenic platinum (II) complex and a carrier to an animal to induce the production of antibody; b) fusing antibody-producing cells from the animal with neoplastic cells such as a murine mydoma; c) screening cellular fusion products to identify hybrid cells producing monoclonal antibody specifically binding platinum (II) complex (e.g. by noting binding to immobilized platinum II complex); and d) cultivating the identified cells to produce monoclonal antibody specifically binding to platinum (II) complex.

An important feature of the present invention involves kits useful for the detection of platinum (II) complex in a biological sample, such as a patient's blood, for example. The form and components of such kits would be to enable practitioners, such as those involved with cancer chemotherapy, to readily monitor the amounts of platinum (II) complex present in a patient. The methods described above and variations thereupon for detection of platinum (II) complex would be the methods enabled by these kits. One kit prototype would comprise: a) a carrier such as a cardboard or plastic box, for example, compartmentalized to receive one or more container means such as vials in close confinement therein; b) a first container means comprising a platinum (II) complex which may be immobilized; and c) a second container means comprising a first monoclonal antibody, for example a murine monoclonal antibody, with a detectable label and specifically binding platinum (II) complex.

The first monoclonal antibody of the kits described herein is the monoclonal antibody of the present invention. The platinum (II) complex in a container means is preferably a may be a DACH-platinum (II) complex.

Another kit useful for the detection of platinum (II) complex in a biological sample would be one which comprises: a) a carrier compartmentalized to receive one or more container means in close confinement therein; b) a first container means comprising a first monoclonal antibody, for example a murine monoclonal antibody, which may be bound to a solid matrix and specifically binds platinum (II) complex; and c) a second container means comprising a platinum (II) complex bearing a detectable label.

According to the present invention a kit useful for the detection of platinum (II) complex in a biological sample may also comprise: a) a carrier compartmentalized to receive one or more container means in close confinement therein; b) a first container means comprising a first monoclonal antibody which specifically binds platinum (II) complex; and c) a second container means comprising a detectably labeled second monoclonal antibody which specifically binds platinum (II) complex.

A kit of the present invention useful for the detection of platinum (II) complex in a biological sample may also comprise: a) a carrier compartmentalized to receive one or more container means in close confinement therein; b) a first container means comprising a first monoclonal antibody of a first isotype which specifically binds platinum (II) complex; c) a second container means comprising a second monoclonal antibody of a second isotype which specifically binds platinum (II) complex; and d) a third container means comprising an antibody specifically binding antibody of the second isotype and bearing a detectable label.

A variation of a kit useful for the detection of platinum (II) complex in a biological sample would comprise: a) a carrier compartmentalized to receive one or more container means in close confinement therein; b) a first container means comprising a first monoclonal antibody specifically binding a platinum (II) complex and being from a first animal; c) a second container means comprising a second monoclonal antibody which specifically binds platinum (II) complex and being from a second animal; and d) a third container means comprising an antibody specifically binding antibody from the second animal and bearing a detectable label.

The present invention also involves methods for preparing and using a tumor-directed platinum (II) complex. These methods comprise a series of steps analogous to those well-known in the art generically. Initially a first monoclonal antibody having binding affinity for the platinum (II) complex is obtained, for example, by immunizing an animal against a platinum (II) complex, preferably against a DACH platinum (II) complex, and fusing antibody-producing cells from the animal with neoplastic cells to form hybridomas. A second monoclonal antibody, preferably murine and having binding specificity for a surface antigen of the tumor may be obtained by standard methods comprising, for example, immunization of an animal against purified tumor surface antigens. The first monoclonal antibody would then be conjugated to the second monoclonal antibody to produce an antibody conjugate. This conjugation is preferably covalent and may involve a bifunctional coupling agent, more preferably a heterobifunctional agent, such as N-succimidiyl-3-(2-pyridyldithio) propionate,m-maleidimido-N-hydroxysuccinimidyl ester, bromoacetyl-p-aminobenzoyl-N-hydroxysuccimidyl ester, bromoacetyl-p-aminobenzoyl-N-hydroxysuccimidyl ester and iodoacetyl-N-hydroxysuccinimidyl ester (see e.g., Ghose et al. J. Nat'l Cancer Inst. Vol. 61 pp 657-676 (1980)). A quantity of the platinum (II) complex would then be added to the antibody conjugate to produce a tumor-directed platinum (II) complex. A method for treatment of animals afflicted with a tumor sensitive to a platinum (II) complex would then comprise the additional step of parenterally administering the tumor-directed platinum complex to the animal in a therapeutically effective amount.

BRIEF DESCRIPTION OF THE DRAWINGS

FIG. 1 is a schematic representation of a hybrid drug-binding:target antigen binding antibody complex involved in delivery of a drug molecule to an antigenbearing cell.

FIG. 2 schematically illustrates the structure of platinum complexes related to the present invention.

FIG. 3 shows that antibody from hybridoma strain $1C_1H_2A_5$ grown both in ascites and in culture media is capable of binding to radiolabeled platinum complex in solution. Equilibrium dialysis was performed with the antibody and Pt complex. Control monoclonal antibody (ABY 96.5 CTR) was unrelated to platinum complex.

FIG. 4 shown the gel permeation HPLC profile of a [$^3$H] Pt/MOAB complex. The absence of free platinum complex after equilibrium dialysis at 4° C. is evident.

DESCRIPTION OF THE PREFERRED EMBODIMENT

Figure 5:
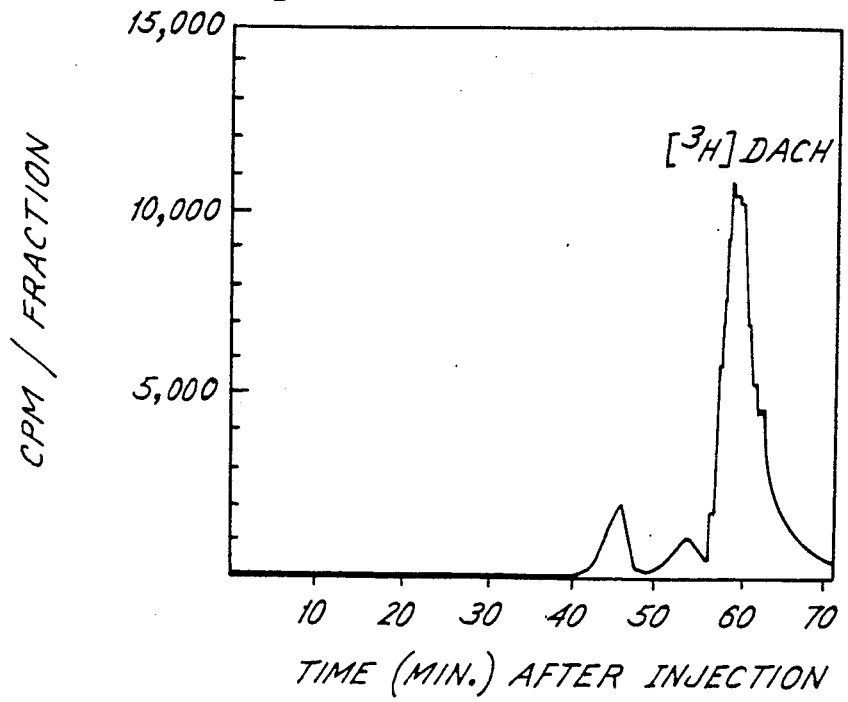
FIG. 5 shows the HPLC gel permeation profile of free [$^3$H] Pt complex.

Platinum (II) complexes are extremely active therapeutic agents highly toxic to both normal and tumor cells alike. Coupled to targeting monoclonal antibodies, drugs and toxins have potential for improved selectivity while simultaneously reduced toxic side effects. However, coupling platinum complexes to monoclonal antibodies by covalent modification of the platinum complexes leads to their inactivation. An alternative means of coupling to an antibody has been developed which employs a monoclonal antibody which reversibly binds to platinum complex in a non-neutralizing manner. This reversible, drug carrier-antibody may be covalently coupled, for example, to a tumor-targeting antibody. While the concept of using antibodies as reversible carriers for therapeutic agents is not new, the application of this approach to platinum complexes and the development of a monoclonal antibody which reversibly binds but does not neutralize the antitumor properties of platinum complexes is new and part of the present invention. A central aim of the present invention involves the creation of a specific delivery system for platinum (II) complexes particularly DACH platinum (II) complexes, in biologically active form which results in specific transport of the complex to a tumor. This system may be created, for example, by covalently conjugating an anti-Pt(II) monoclonal antibody to a monoclonal antibody having specific affinity for a tumor surface antigen. The platinum complex will be maintained in stable active form for specific delivery to the antigen-bearing tumor when a combination of Pt(II) non covalently bound to the conjugate is parenterally administered.

As indicated above, the present invention, in one embodiment, involves a combination between a therapeutically active platinum complex with a monoclonal antibody selected to bind the platinum complex in a manner which does not materially impair its therapeutic activity but which forms a combinant with the complex to confer upon the complex an in vivo serum half-life longer than that of the therapeutic agent alone. Alternatively, although not preferred, the invention could comprise a similar combination of platinum complex with polyclonal antibodies selected to bind the platinum complex without materially impairing its therapeutic activity and which form a combinant having an extended serum half-life as compared to free platinum (II) complex.

In another embodiment, the present invention comprises a process involving the administration to a host of a therapeutic platinum complex combined with either a monoclonal antibody or polyclonal antibodies having the properties noted above. The processes of the present invention may also include either simultaneous administration of the therapeutic platinum complex and a suitable antibody preparation or an initial administration of the antibody preparation followed by administration of the therapeutic agent after the antibody has had an opportunity to distribute itself throughout the host.

The therapeutic platinum complexes most useful in the invention are those which are or can be made immunogenic, i.e., those for which an immune response can be obtained either directly or, in the case of a hapten, by binding the agent to a molecule which is immunogenic. Monoclonal antibodies against the therapeutic agent can be obtained by methods which are now well known to the art and which need not be described in detail. These methods generally involve immunization of a mouse or other animal species, usually mammalian or avian, with the immunogen. After an immune response is generated, spleen cells of the immunized mouse are fused with cells of an established lympoid tumor line using known techniques to form hydridomas which produce monoclonal antibodies. Clones of hydridomas are screened to select those which are producing monoclonal antibodies that are specific for the antigen of choice, in this case a therapeutic platinum complex. Monoclonal antibodies having the desired specificity are further screened to select those that form an antibody Pt complex combination in which the complex retains all, or substantially all, of its therapeutic activity. These combinations may be further screened to select those which have an extended serum half-life. In certain circumstances, it may be beneficial to use a mixture of two or more monoclonal antibodies. In some circumstances it may also be desirable to use a stoichiometric excess of antibody.

The in vitro immunization of lymphocytic cells and eventual fusing to form hybridomas has been accomplished by others and is considered within the scope of the present invention (Pardue, 1983, J. Cell. Biol., V 96, pp 1149–1154).

Polyclonal antibodies conceivably useful in the invention may be obtained by well known techniques as well. These include stimulating an immune response against a platinum (II) complex, or fragment thereof, in a suitable animal host such as a rabbit or other mammal. Chickens and other avian species may also be used. Serum taken from the host is subjected to affinity purification to isolate polyclonal antibodies against the therapeutic agent. These antibodies are subsequently fractionated, if necessary, to isolate a subpopulation which complexes with the therapeutic agent without materially impairing its desirable activity.

Murine monoclonal antibodies are most readily produced and used in the practices of the present invention. Particularly preferred for future uses in this invention are human antibodies against platinum (II) complex therapeutic agent. These human antibodies may be produced by hybridomas which, for example, are products of fusion between a B-lymphocyte obtained, for example, from a human appropriately immunized and an established mammalian lymphoid line, e.g., a human or mouse myeloma line.

As used herein, the term antibody includes fragments thereof such as Fab, Fab, and Fab,2 or mixtures thereof and including mixtures with whole antibody. Such fractions may be less immunogenic in some patients and may also better allow better penetration of the agent to the target site.

In certain applications mentioned above, the monoclonal antibody may be a hybrid or more than one antibody having a dual specificity, one specificity for finding a therapeutic platinum (II) complex and the other specificity for binding against another antigen, for example, an antigen associated with site of disease where it is desired to optimize delivery of the agent. These sites may involve tumor associated antigens such as carcinoembryonic antigen (CEA), prostatic acid phosphatase (PAP, ferritin and prostate specific antigen (PSA). In such cases, the other specificity could be selected to bind with a platinum complex which has anti-tumor activity.

These examples are presented to describe a best mode, preferred embodiments and utilities and are not meant to limit the present invention unless otherwise stated in the claims appended hereto.

EXAMPLE 1

Production of Monoclonal Antibody (MOAB) Binding Platinum Complexes

The basic procedure of monoclonal antibody production was followed in James W. Goding's "Antibody Production by Hybridoma", Journal of Immunological Methods. 39 (1980) 285–308.

Immunization of Animals

Deoxyribonucleic acid-cellulose (DNA/cellulose, Sigma Chemical Co.) was obtained. The DNA/cellulose was washed thrice with distilled water and centrifuged to form a pellet. A disodium 1,2-diaminocyclohexane platinum sulfate complex (DACH/Pt) was dissolved in 1 ml of distilled water. The DACH/Pt solution was added to the pellet of DNA/cellulose, mixed and allowed to react overnight at 4. C. The DACH/Pt-DNA/cellulose product was washed thrice with distilled water and pelleted by centrifugation. To the pellet was added 0.25 ml of $H_2O$ and 0.75 ml of adjuvant. Freund's complete adjuvant was used for the first immunization and incomplete Freund's adjuvant for all subsequent injections.

BALB/C mice (females, 6–8 weeks old) were used for the production of antibody against platinum complex. Immunization doses were prepared for three animals. The immunization dose per animal was 2 mg of DACH/Pt with 10 mg of DNA/cellulose.

The first immunization was given intraperitoneally and all follow-up injections were intramuscular. All animals were given one shot/week for 3 weeks, rested 2 weeks and given one booster shot before checking for antibody production. A few drops of blood were obtained for testing of antibody production. An antibody titer of 1:6,400 to 1:12,000 was obtained (tail vein blood sample) before a fusion was considered. Three days prior to fusion of spleen cells from the animal, DACH/Pt DNA/cellulose (200 ug/ml) in saline was administered by tail vein injection.

Fusion of Myeloma Cells to Splenic Lymphocytes

A mouse which produced high antibody titer was selected and the spleen removed in a sterile fashion. The spleen was immediately transferred to a small sterile Petri dish containing 5 ml of fusion medium. The medium for the fusion was Iscove's (Hazleton Research Products, Inc.) with 10% normal horse serum and antibiotics of penicillin/streptomycin/fungizone solution (5 ml/500 ml bottle). Once under a tissue culture hood, the spleen was transferred to a second petri dish containing 5 ml of the Iscove's medium. The spleen was minced by teasing with the use of two 18g needles (holding the spleen with one needle and teasing with the other). Cells were seen coming out of the spleen. The cell suspension was transferred to a 15 ml conical centrifuge tube and allowed to settle for 10 minutes. The cell suspension was then transferred to another 15 ml tube with care to avoid tissue or cell clumps. The cell suspension (20 ml) and mix was removed and treated with Trypan blue for counting and viability. The cell suspension was centrifuged for 10 minutes at 1200 rpm.

A non-secretor myeloma cell line ($P_3$-NS1-Ag4–1) was obtained from a commercial source. These $P_3$ cells were maintained in log phase growth at low density. On the day prior to fusion, the $P_3$ cells were split and suspended at a density of $5 \times 10^5$ cell/ml. The $P_3$ cells should have a growth rate resulting in overnight doubling.

At this time, myeloma $P_3$ cells which had been maintained in log phase growth were transferred to a 50 ml centrifuge tube to be pelleted and combined—the combined cells were then centrifuged at 1200 rpm for 10 minutes. A typical fusion required around $10^8$ myeloma cells and a similar number of spenic lymphocytes. One should have a 10:6 ($P_3$ spleen) ratio or better to optimize results. A viability of 95–100% is recommended both cell types to obtain a successful fusion.

One day prior to fusion, monocyte feeder layers had been prepared as follows: Two BALB/C mice were killed and their peritoneal cavities flushed with 5 ml of sucrose solution (11.6%). Cells obtained from these peritoneal lavages were washed in complete Iscove's medium and centrifuged. The cell pellet was resuspended to 100 ml in complete Iscove's medium, distributed in ten 96-well plates at 100 ul/well and incubated at 37° C. in a $CO_2$ incubator.

Polyethylene glycol (PEG) was purchased from Polyscience, Inc. (Cat. # 0678, MW 4000). The PEG was weighed, sterilized by autoclaving, allowed to cool to about 80° C. (at which temperature it was liquid), and an appropriate volume of sterile culture medium without serum added. The final percentage (P) of PEG was calculated with sufficient accuracy by the formula $$P = \frac{100\,m}{M + V}$$

Where (M) is the weight of PEG in grams and (V) is the volume of medium added.

Example: M=4 gms.

$$40\% = \frac{100(4)}{4 + V}$$

$$V = \frac{400 - 160}{40}$$

or $$V = 6 \text{ ml}$$

The PEG solution should remain for 4 days at 4° C. before being used in the fusion but may be stored at room temperature.

The $P_3$ cells and spleen cell (at an adjusted ratio) were combined in a 50 ml tube, topped with media, washed and centrifuged at 1200 rpm for 10 minutes to form a pellet. A desired concentration of 600 cells/well was used for plating.

The most sensitive step was next: adding 40% PEG. PEG apparently changes the membrane density and may enduce cells to fuse because their cell membrane is not intact. The pellet supernatant was removed from the centrifuged cell mixture and the pellet resuspended. Two ml of warm (37° C.) PEG was added over a 30 second period while gently shaking the tube to resuspend the cells. The shaking was continued for 45 seconds at 37.C. After centrifugation for 40 sec at 800 RPM, 10 ml of Iscove's medium was added drip-wise to the mixture. At the same time, gentle shaking of the tube was continued. This process very carefully diluted the PEG concentration without shocking the fused membranes. After the addition of the 10 ml, the volume was raised to 50 ml, the tube inverted very carefully to mix and then the cells allowed to rest for a few minutes. After a 10 minute centrifugation at 1200 rpm the supernantant was discarded. To mix, the pellet was inverted slowly, washed with Iscove's medium and again inverted slowly. After a 10 minute centrifugation at 1200 rpm the supernatant was discarded. The pellet was resuspended to 50 or 100 ml in Iscove's medium+HAT.

One mouse spleen yielded sufficient cells to plate 100 ul/well on five 96-well plates—approximately $1 \times 10^4$ cells/well. HAT was added only to the completed fusion before plating on a monocyte feeder layer. HAT media was used for feeding cultures until transferral to 6-well plates. The A-(aminopterin) was removed and feeding continued to HT (hypoxanthine and thymidine) for several more days before reversion to Iscove's media. After 2 or more clonings, cells were "weaned" off fetal calf serum and serum-free media added (Nutridoma-NU) BoehringerMannhaeim Biochemical Co.

The PEG-treated cells (100 ul) were plated on top of the monocyte feeder layer and returned to an incubator undisturbed for several days. Hybrids were usually not observed for at least seven days. Plates should not be fed until some colonies of hybrids are observed. Screening and testing was done on the supernatant in wells where hybrids were produced. A monocyte feeder layer is sometimes needed when transferring the hybrids from the 96-Well plate to the 24 or 6-well plates. HAT media is used until it is certain that all parental myeloma cells are dead. The cells were weaned by first removing "A", and the "HT" by the time the hybrids were grown sufficiently to be put into T-25 culture flasks.

Screening Procedures

A preliminary screen procedure was accomplished by enzyme-linked immunosorbent assay (ELISA). A Hybridoma Screening Kit produced by BRL (Bethesda Research Laboratories) was used for screening with modification made for testing Pt complex. Falcon # 3912 flexible microtest 96-well plates were used. Calf thymus DNA 50 ul, 100 ug/ml in distilled $H_2O$ was added to the wells and dried overnight at 37° C. To half the dried plates, 50 ul of the platinum (II) complex, DACH-platinum-$SO_4^{-2}$, was added to each well and dried overnight at 37° C. The platinum complex 100 ul/ml was prepared in distilled $H_2O$ and pH adjusted to 7.0 by adding 1.5 ul of NaOH per mg of platinum. The platinum was made up immediately before plating.

Plates were coated on day of test by adding 50 ul of PBS containing 10% goat serum for 15 minutes. From 50-100 ul of hybridoma culture supernatant was added to the wells of both DNA and DNA-DACH/Pt plates and incubated for 3 hours at 4° C. A control of spent media was added to each plate. After incubation, plates were washed 4 x in PBS, pH 7.2+1% goat serum. B-galactosidase—conjugated goat anti-mouse antibody 1:200 dilution in PBS containing 1% goat serum (BRL—reagent) 50 ul was added and the plates were incubated 1 hour at room temperature and washed 4 times with PBS. The chromophoric substrate p-nitrophenyl glucose (PNPG) (1mg/ml in 5o mM sodium phosphate, pH7.0 with 1.5 mM $MgCL_2$—BRL kit) was added at 50 ul per well after incubation for one hour at 37° C. followed by quenching or stopping the reaction by addition of 50ul/well of 0.5 M $Na_2CO_3$. The wells were read at OD 410 on a ELISA plate reader. A positive reaction was indicated by the development of a yellow color in well.

Cloning

As soon as positive wells were identified, it was advisable to clone the cells. Frozen bulk cultures very seldom grow out positive clones because they are overgrown by irrelevant cells. The first cloning may result in only a small percentage of active cells due to chromosome loss; however, recloning increased active cells as well as cloning efficiency. The first cloning should preferably be plated at 2, 1 and 0.5 cells/well. However, recloning should be done at 0.5 to 0.3 cells/well. This will help insure that clones will be only one clone/well and hopefully only one resultant isotype. Cells should be frozen away for positive clones (1 to $10 \times 10^6$ cell in PBS+10% DMSO) as soon as possible because many clones become less active or lose activity over several generations in culture. Positive clones are recognized by the same screening method as described for the hybridomas. Isotyping should be performed on clones selected for production of monoclonal antibody.

Isotyping

Isotyping was done by using the Boehringer Mannheim Biochemicals—mouse immunoglobulin subtype identification kit. Two antigens were used to coat the plates. Cappel's affinity purified goat anti-mouse IgG-heavy and light chain at a 1:50 dilution in $H_2O$. The second antigen was the DACH/Pt at a concentration of 100 ul/ml, prepared by the same method as for the screening test.

Large Scale Culture and MoAb Production

Once the hybridoma cells have been successfully cloned, they may be and were grown in bulk. Cultures were expanded gradually, especially in the early phases. Some hybrids were particularly intolerant of dilutions. Typical antibody concentrations that may be achieved in culture supernatants were 10–100 ul/ml. At this point, the cells were usually converted to a serum free environment. The horse serum-containing medium was replaced with Nutridoma-NU (Boehringer-Mannheim). The cultures were checked weekly by ELISA to insure that they were continuing to produce antibody. Whenever supernatant was collected, the cells were frozen in liquid $N_2$ for subsequent rejuvenation of clones. Supernatant was concentrated and purified for MoAb production.

Bulk cultures were also grown for MOAB production by ascites. Since a liter of culture fluid yields about 50 mg of antibody, growth in mice allowed much greater production (from 3–15 mg/ml for IgG-IgM rather lower).

Usually $10^7$ hybridoma cells were administered intraperitoneally to each mouse. The mice had been Pristane-primed with 0.5 ml at least 1 week prior to injection of cells. Evidence of substantial cell growth usually appeared in 2 to 4 weeks. If tumors failed to appear-light irradiation, (350 R) was administered to the mice just before injection with cells.

EXAMPLE 2

MONOCLONAL ANTIBODIES PRODUCED

Five different antibodies were produced which bound to platinum complex as assessed by ELISA assay (Table 1). Competitive binding studies were performed using an ELISA assay system for antibody and increasing the amount of methyliminodiacetato-1,2-diaminocyclohexane platium (II) complex (MIDP) added to wells pre-coated with platinum MIDP. The concentrations of added MIDP required to block antibody binding to the MIDP-coated plate by 50% is shown in Table 1. The highest concentration of MIDP was required for antibody $1C_1H_2A_5$. The lowest concentration was 0.65 ug for antibody $3A_6B_1$.

TABLE 1

| CHARACTERIZATION OF PLATINUM ANTIBODIES | | | |
|---|---|---|---|
| Antibody Designation | Sub-Type | MIDP* Conc. for 50% Inhib. | MIDP** Binding |
| $3A_2A_1$ | $IgG_3$ | 1 ug | + |
| $1C_1H_2A_5$ | IgM | 1.5 ug | + |
| $3A_6A_2$ | IgM | 1 ug | + |
| $3A_6B_1$ | IgG | 0.65 ug | + |

TABLE 1-continued

| CHARACTERIZATION OF PLATINUM ANTIBODIES | | | |
|---|---|---|---|
| Antibody Designation | Sub-Type | MIDP* Conc. for 50% Inhib. | MIDP** Binding |
| 1B₁ | IgG | N.D. | ++ |

N.D. - Not determined
*Concentration of MIDP required to compete for 50% of binding of platinum antibody to platinum-complex coated 96-well plates. These values give a relative assessment of the affinity of the antibody for the platinum complex. That is, higher concentrations of MIDP added will be required to inhibit 50% of antibody binding for a high affinity antibody compared to an antibody with lower affinity.
**Relative scale of binding to MIDP from no binding (0) to positive (+) to strongly positive (++).

EXAMPLE 3

Characterization of Antibody From Hybridoma Strain $1C_1H_2A_5$

Antibody $1C_1H_2A_5$ was prepared either from spent hybridoma culture media or as an ascites in Balb/C mice. The antibody was incubated with $800 \times 10^3$ CPM of [$^3$H] labeled platinum complex for 24 hrs and then dialyzed for 4 hrs against PBS and counted to determine [$^3$H] activity. As shown in FIG. 3, the $1C_1H_2A_5$ monoclonal antibody, from either ascites fluid or ammonium-sulfate precipitated culture medium, contained 12–14 fold greater [$^3$H] label than control antibody. Analysis of the [$^3$H] label by HPLC showed that there was no free [$^3$H] platinum complex (FIG. 4). In addition, the [$^3$H] label was found at a molecular weight corresponding to 160,000 Daltons. The HPLC elution profile of free platinum complex is shown in FIG. 5.

EXAMPLE 4

Antitumor Toxicity

Figure 6:
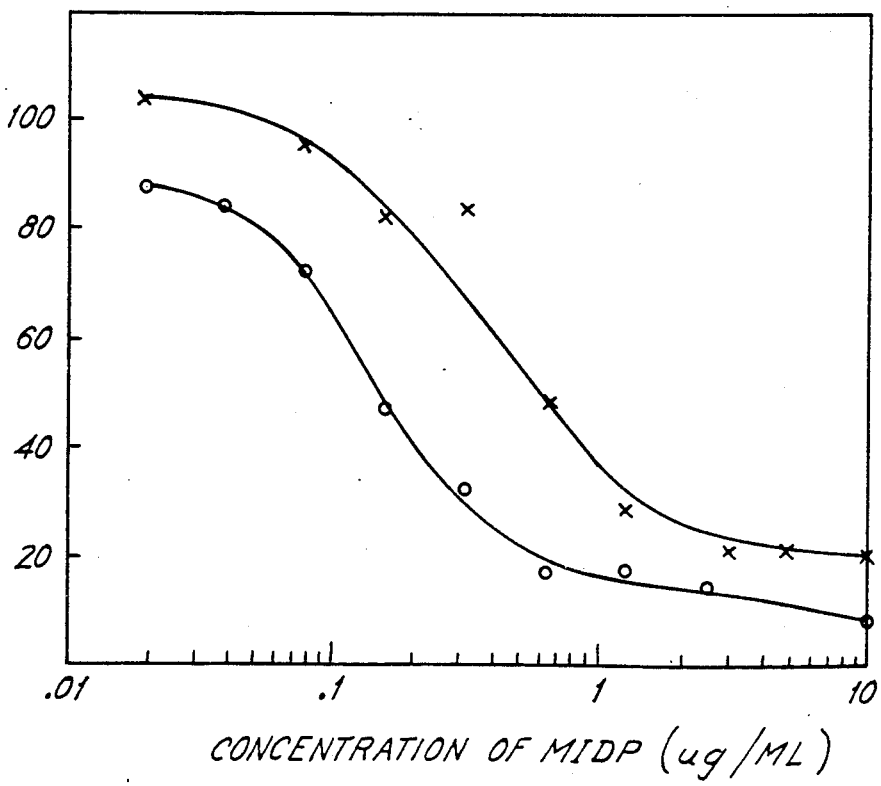
FIG. 6 shows an in vitro dose response assay for MIDP toxicity (O) MIDP-MOAB complex toxicity (X) toward MCF-7 cells (72 hr exposure). Eight thousand MCF-7 cells were seeded per well and an MTT dye viability test performed.
Figure 7:
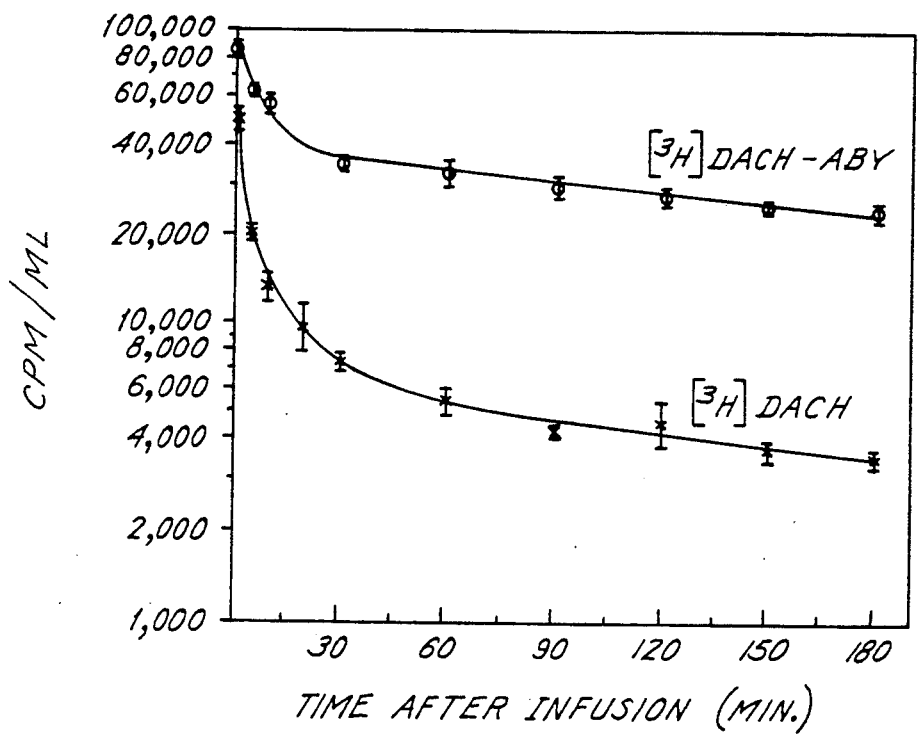
FIG. 7 shows the relative levels of blood-bourne [$^3$H] DACH Pt when free [$^3$H] DACH Pt (X) was administered intravenously to a rat and blood-bourne [$^3$H] DACH Pt when a MOAB/[$^3$H] DACH Pt combinant (O) was intravenously administered to a rat.

In order to determine whether the MIDP/MOAB complex retained antiproliferative activity against cells in culture, the antibody (2 mg) was incubated with 200 ug of MIDP platinum complex for 24 hrs. The MOAB/MIDP solution was then dialyzed for 4 hrs at 4° C. against phosphate-buffered saline (PBS). The dialysate was then analyzed for total platinum by atomic absorption spectrometry. The monoclonal antibody/MIDP complex was then added to human breast carcinoma cells (MCF-7) in concentrations between 0.01 and 10 ug Pt/ml. As a control on the same plates, MIDP was also added at equal platinum concentrations. At 72 hrs after treatment, the wells were assessed for viable cells by MTT assay. As shown in Table 2, both MIDP and MIDP/MOAB preparations were capable of inhibiting the growth of MCF-7 cells. The concentration of MIDP/MOAB complex required for 50% inhibition of cell growth was 4 fold higher than that required for MIDP alone (0.6 ug/ml for MIDP/ABY to 0.15 ug/ml for MIDP alone) suggesting a slight diminution of antiproliferative activity of the MIDP complex. FIG. 6 shows the dose and response profile of the MCF-7 cells to free MIDP and MIDP/MOAB.

TABLE 2

| MTT Assay; Cytotoxicity of MIDP and MIDP-MOAB complex on MCF-7 breast carcinoma cells* | | |
|---|---|---|
| MIDP concentration (ug/ml) | Percent of Control Cell survival** | |
| | MIDP alone | MIDP-MOAB complex |
| 10 | 8.3 | 21.4 |
| 5 | 10.8 | 21.9 |
| 2.5 | 15.2 | 21.7 |
| 1.25 | 18.5 | 29.4 |
| 0.625 | 17.0 | 48.8 |
| 0.312 | 32.3 | 83.4 |
| 0.156 | 45.5 | 82.0 |
| 0.078 | 72.4 | 95.3 |
| 0.039 | 84.3 | 115.0 |
| 0.019 | 86.9 | 104.0 |

*This experiment was performed once in quadruplicate and the values shown are the mean values.
**Cell survival was determined using the tetrazolium dye-binding method (MTT) which dye reacts only with living cells.

EXAMPLE 5

Pharmacokinetic Study and Tissue Distribution

A pharmacokinetic study of [$^3$H] DACH-Pt compared to [$^3$H] DACH-Pt bound to monoclonal antibody $1C_1H_2A_5$ was performed. A small amount of IgM antibody was purified and allowed to reach with [$^3$H] DACH-Pt overnight at 5°. Excess [$^3$H] DACH-Pt was removed by equilibrium dialysis for 4 hr. Rats were anesthetized and intravenously administered [$^3$H] Pt complex. Blood samples were taken at various times after administration of either [$^3$H] DACH-Pt (3 animals) or the same [$^3$H] dose of [$^3$H] content. As seen in FIG. 5 the clearance of drug itself from plasma fit a triphasic curve (t1/2 alpha=1.24 min, t1/2 beta-fit 10.2 min, t1/2 gamma=243 min). The plasma clearance Pt/MOAB complex also fit a triphasic curve for clearance (t1/2 alpha=5.21 min, t1/2 beta=26 min, t1/2 gamma=291 min) which was quite different than that found for the free drug. The area under the concentration curve (AUC) for Pt/MOAB complex was 7-fold higher than that found for free drug, suggesting reduced tissue distribution of the antibody/drug complex. The tissue disposition data shown in FIG. 8 and 9 confirm that the antibody inhibited the platinum from distributing to kidney, small intestine and liver as well as other organs.

This study showed that the pharmacology of platinum (II) complex may be substantially modified using a monoclonal antibody, thus suppressing the distribution of drug to sites for toxicity (liver, kidney and small intestine, for example) and increasing the circulation time of active agent. In vitro studies of the druganti-body complex described earlier herein showed that the dose-response curve for antiproliferative effect against MCF-7 cells was similar to that for free drug, thereby demonstrating that the antibody-drug complex retained essentially full antitumor activity.

EXAMPLE 6

Figure 10:
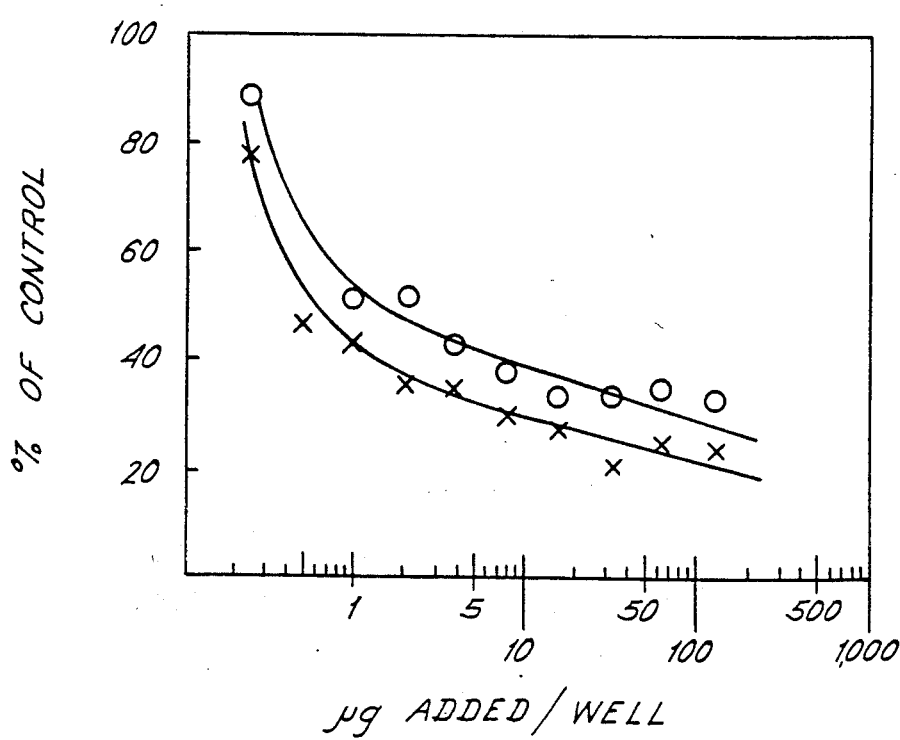
FIG. 10 shows the competition of MIDP (X) and Pt complex A (MIDP in retrospect) (O) for binding to MOAB from hybridoma $1C_1J_2A_5$. A DACH Pt complex was immobilized on the surface of microtiter wells.
Figure 11:
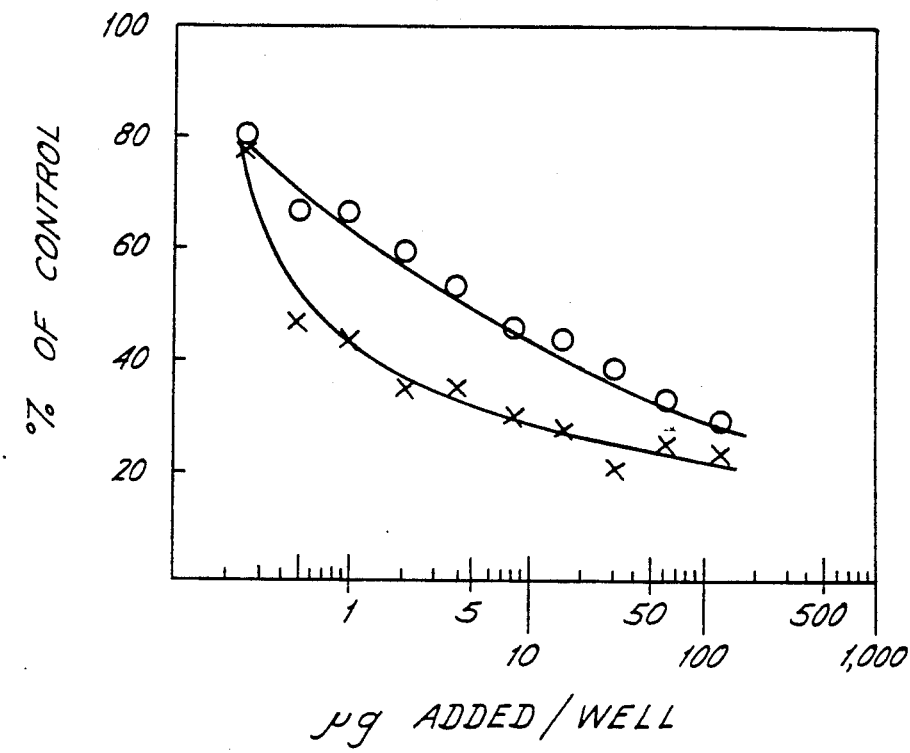
FIG. 11 shows the competition of MIDP (X) and DACH Pt (II)1,1-dicarboxylatocyclobutane (O) for binding to MOAB from hybridoma $1C_1H_2A_5$. A DACH Pt complex was immobilized on the surface of microtiter wells.
Figure 12:
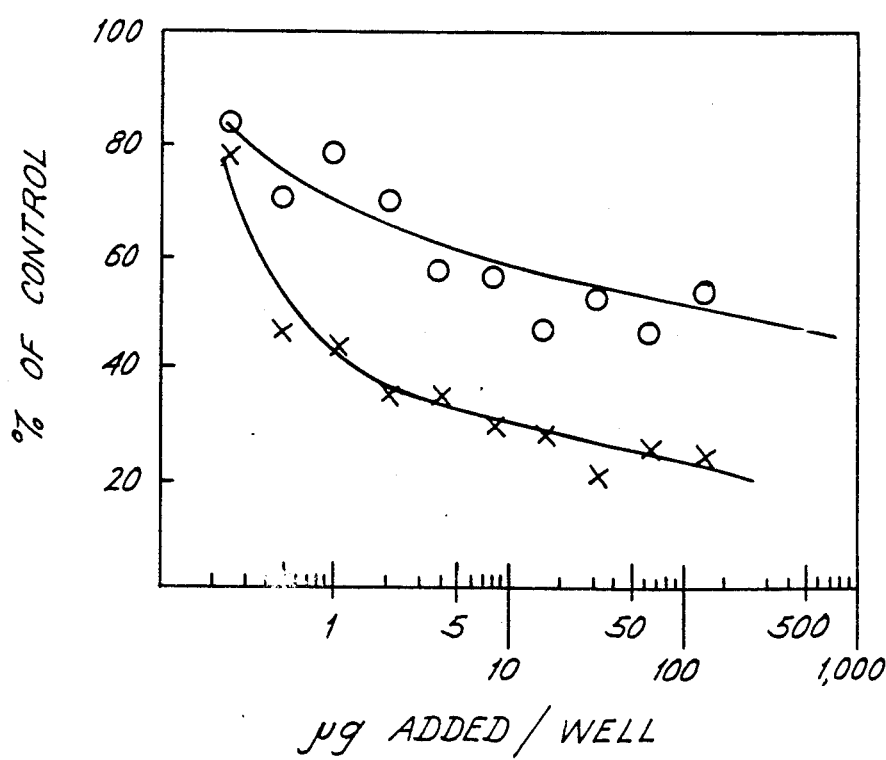
FIG. 12 shows the competition of MIDP (X) and diamine Pt(II)1,1-dicarboxylatocyclobutane (O) for binding to MOAB from hybridoma $1C_1H_2A_5$. A DACH Pt complex was immobilized on the surface of microtiter wells, to which MOAB binding was measured.

Competition of Platinum Compounds In Binding to $1C_1H_2A_5$ Monoclonal Antibody A competitive ELISA assay using monoclonal antibody specific for platinum (II) complex was performed. Monoclonal antibody from hybridoma $1C_1H_2A_5$ was added to microtiter wells having an immobilized DACH Pt complex. The MOAB was added either with no free platinum complex (control) or with increasing amounts of free MIDP platinum complex. Additionally, three compounds (designated A, B and C), whose identities were best unknown at that time, were added in parallel to the MIDP competition study. As shown in FIG. 10 the competition of compound A was quite similar to that of MIDP. Compound B (FIG. 11) was less similar to MIDP and compound C (FIG. 12) was least like MIDP although still being inhibitory of MOAB binding. The concentration of each agent which decreased the antibody binding to 50% of control was: MIDP=1ug; A=2ug; B=4ug and C=200ug.

Figure 8:
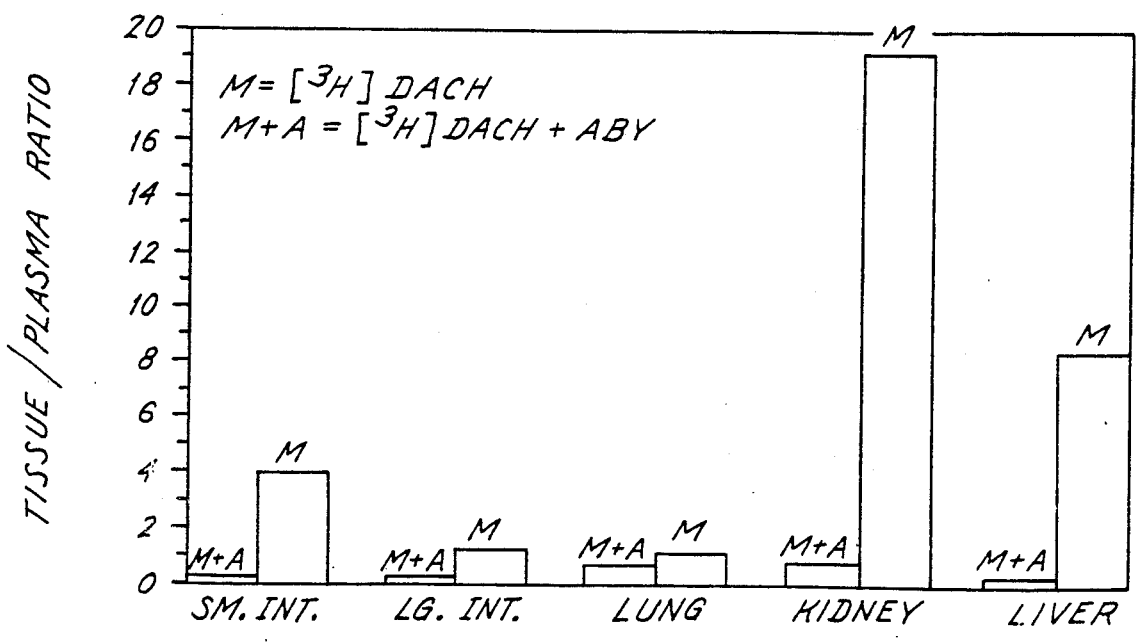
FIG. 8 shows the tissue to plasma distribution ratio of [$^3$H] DACH Pt for rat from small intestine, large intestine, lung, kidney or liver three hours after administration of free [$^3$H] DACH Pt complex (M) or a MOAB [$^3$H ] DACH combinant (M+A).
Figure 9:
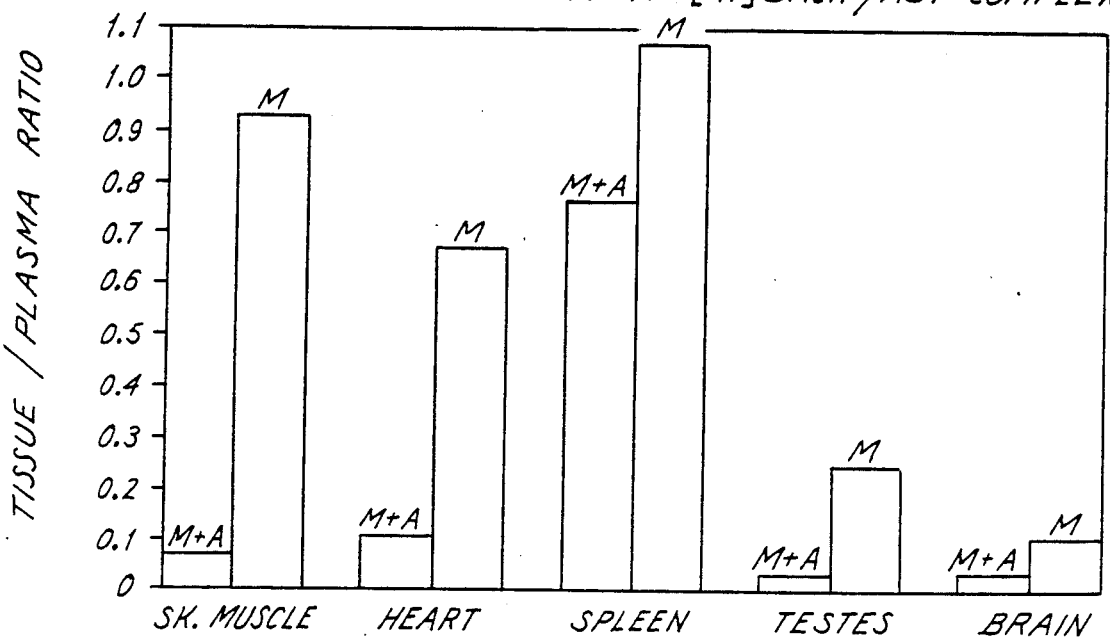
FIG. 9 shows the tissue to plasma distribution ratio of [$^3$H] DACH Pt found in rat skeletal muscle, heart, spleen, testes and brain three hours after administration of free [$^3$H] DACH Pt complex (M) or a MOAB [$^3$H] DACH combinant (M+A).

On breaking the code for the samples, A was in fact MIDP. Compound B was a DACH-platinum compound with a different leaving group on the platinum, namely B was DACH Pt(II) 1,1-dicarboxylatocyclobutane. Compound C was diamine Pt(II) 1,1-dicarboxylatocyclobutane. As shown in FIGS. 8-10, while the antibody recognized compound C, it took 100-200 times more of compound C to compete at a level with MIDP. Compound B, with the same leaving group as compound C (1,1-dicarboxylatocyclobutane), but with a DACH substituent instead of two amine groups, bound to the antibody about 50 fold more effectively than compound C. This relationship of chemical structure to binding affinity was consistent with a major epitopic contribution by the DACH to the MIDP-antibody interactions.

The MOAB of the present invention, as exemplified above, show significant affinity for platinum (II) complexes, particularly when the complexes have an organic stable ligand and/or an alkylamine substituent such as DACH, for example.

x x x x x x x x x

Changes may be made in the construction, operation and arrangement of the various parts, elements, steps and procedures described herein without departing from the concept and scope of the invention as defined in the following claims.

What is claimed is:

1. A cell line resulting from fusion of a neoplastic cell with an antibody-producing animal cell obtained from an animal immunized against a platinum (II) complex, said cell line forming a monoclonal antibody specifically binding platinum (II) complex in competition with an antibody produced by hybridoma strain $1C_1H_2A_5$ having ATCC accession number HB 9411, strain $3A_2A_1$, strain $1A_6A_2$, strain $3A_6B_1$ or strain $1B_1$.

2. The cell line of claim 1 defined further as being a continuous murine hybridoma cell line which secretes recoverable quantities of monoclonal antibody.

3. The cell line of claim 1 wherein the monoclonal antibody is of an IgG or IgM isotype.

4. The cell line of claim 1 wherein the neoplastic cell is a myeloma cell.

5. The cell line of claim 1 wherein the antibodyproducing animal cell is a splenic cell.

6. The cell line of claim 1 wherein the animal is immunized with a conjugate of a platinum (II) complex and a macromolecular species.

7. The cell line of claim 6 wherein the macromolecular species is a polynucleotide.

8. The cell line of claim 7 wherein the polynucleotide is DNA.

9. The cell line of claim 7 wherein the macromolecular species is a protein.

10. The cell line of claim 1 defined further as being hybridoma strain $1C_1H_2A_5$ having ATCC accession number HB 9411, strain $3A_2A_1$, strain $1A_6A_2$, strain $3A_6B_1$ or strain $1B_1$.

11. The cell line of claim 1 wherein the platinum (II) complex is a DACH-platinum (II) complex.

12. A murine hybridoma cell line producing recoverable quantities of a monoclonal antibody which specifically binds a platinum (II) complex.

13. The murine hybridoma cell line of claim 12 wherein the monoclonal antibody is of an IgG or IgM isotype.

14. The murine hybridoma cell line of claim 12 defined further as produced by a process involving immunization of a mouse against platinum (II) complex coupled to a carrier and fusion of antibody-producing cells from said animal with a neoplastic murine cell line.

15. The murine hybridoma cell line of claim 12 wherein the platinum (II) complex is a DACH-platinum (II) complex.

16. A composition of matter comprising a monoclonal antibody specifically binding a platinum (II) complex.

17. The composition of matter of claim 16 wherein the monoclonal antibody is defined further as binding a platinum (II) complex in competition with an antibody produced by hybridoma strain $1C_1H_2A_5$ having ATCC accession number HB 9411, strain $3A_2A_1$, strain $1A_6A_2$, strain 3 $A_6B_1$ or strain $1B_1$.

18. The composition of matter of claim 16 wherein the monoclonal antibody is defined further as being an antibody produced by hybridoma strain $1C_1H_2A_5$ having ATCC accession number HB 9411, strain $3A_2A_1$, strain $1A_6A_2$, strain $3A_6B_1$ or strain $1B_1$.

19. The composition of matter of claim 16 wherein the monoclonal antibody is defined further as being of an IgG or IgM isotype.

20. The composition of matter of claim 16 wherein the platinum (II) complex is a DACH-platinum (II) complex.

* * * * *

UNITED STATES PATENT AND TRADEMARK OFFICE
CERTIFICATE OF CORRECTION

PATENT NO. : 5,053,226

DATED : October 1, 1991

INVENTOR(S) : Michael G. Rosenblum et al.

It is certified that error appears in the above-identified patent and that said Letters Patent is hereby corrected as shown below:

In claim 5, column 22, line 3, delete the term "antibodyproducing" and insert the term --antibody-producing-- therefor.

In claim 17, column 22, line 42 delete the term "3 $A_6B_1$" and insert the term --$3A_6B_1$-- therefor.

Signed and Sealed this

Second Day of February, 1993

Attest:

STEPHEN G. KUNIN

Attesting Officer

Acting Commissioner of Patents and Trademarks